(12) United States Patent
Delavault et al.

(10) Patent No.: US 8,034,808 B2
(45) Date of Patent: Oct. 11, 2011

(54) THERAPEUTIC COMPOSITIONS CONTAINING AT LEAST ONE PYRROLOBENZODIAZEPINE DERIVATIVE AND FLUDARABINE

(75) Inventors: Patrick Delavault, Colombes (FR); Chris Pepper, Penarth (GB)

(73) Assignee: Ipsen Pharma S.A.S., Boulogne Billancourt (FR)

( * ) Notice: Subject to any disclaimer, the term of this patent is extended or adjusted under 35 U.S.C. 154(b) by 0 days.

(21) Appl. No.: 11/587,962

(22) PCT Filed: Apr. 26, 2005

(86) PCT No.: PCT/FR2005/001025
§ 371 (c)(1),
(2), (4) Date: Oct. 27, 2006

(87) PCT Pub. No.: WO2005/105113
PCT Pub. Date: Nov. 10, 2005

(65) Prior Publication Data
US 2007/0232592 A1 Oct. 4, 2007

(30) Foreign Application Priority Data
Apr. 27, 2004 (FR) .................................... 04 04424

(51) Int. Cl.
A61K 31/5513 (2006.01)
A61K 31/7076 (2006.01)
A61P 35/00 (2006.01)

(52) U.S. Cl. ..................................... 514/220; 514/263.1
(58) Field of Classification Search .................. None
See application file for complete search history.

(56) References Cited

U.S. PATENT DOCUMENTS
7,511,032 B2  3/2009  Liu et al.

FOREIGN PATENT DOCUMENTS
WO  WO 00/12508  * 3/2000
WO  WO 2005/105113 A3  11/2005

OTHER PUBLICATIONS

Johnson, S.A.: Purine Analogues in the management of lymphoproliferative disease. vol. 8, p. 289-296, 1996.*
Jordan et al.: Molecular mechanisms involved in cisplatin cytotoxicity. Cell Mol Life Sci, 57 (8-9):1229-1235, 2000, abstract only.*
Gregson et al.: Design, synthesis, and evaluation of a novel pyrrolobenzodiazepine DNA-interactive agent with highly efficient corss-linking ability and potent cytotoxicity. J Med Chem, 44:737-748, 2001.*
Johnson: Purine Analogues in the management of lymphoproliferative diseases. Clinical Oncology, 8:289-296, 1996.*
Ross et al.: Fludarabine, A review of its pharmacological properties and therapeutic potential in malignancy. Drug, 45(5):737-759, 1993.*

Written Opinion of the International Searching Authority (Form PCT/ISA/237) issued in International Application No. PCT/FR2005/001025.
S.J. Gregson et al., "Synthesis of a novel C2/C2'-exo unsaturated pyrrolobenzodiazepine cross-linking agent with remarkable DNA binding affinity and cytotoxicity," *Chemical Communications, Journal of the Chemical Society*, pp. 797-798 (1999).
G.P. Wilkinson et al., "Pharmacokinetics and intracellular pharmacological characteristics of the novel pyrrolobenzodiazepine (PDB) dimer SJG-136," *Proceedings of the 94th American Association for Cancer Research Annual Meeting*, vol. 44 (Abstract) p. 320 (Jul. 11-14, 2003).
M.C. Alley et al., "Efficacy evaluations of SJG-136 (NCS 694501), A novel pyrroloben-zodiazepine dimer with broad spectrum antitumor activity," *Proceedings of the 93rd American Association for Cancer Research Annual Meeting*, vol. 43 (Abstract) p. 63 (Apr. 6-10, 2002).
J.A. Hartley et al., "In vitro antitumor activity and in vivo DNA interstrand crosslinking by the novel pyrrolobenzodiazepine dimer SJG-136 (NSC 694501)," *Proceedings of the 93rd American Association for Cancer Research Annual Meeting*, vol. 43 (Abstract) p. 489 (Apr. 6-10, 2002).
P.H. Clingen et al., "The role of nucleotide excision repair and homologous recombination in the sensitivity of mammalian cells to the minor groove crosslinking pyrrolo(2,1-c)(1,4)benzodiazepine dimer SJG-136 (NSC 694501)," *Proceedings of the 94th American Association for Cancer Research Annual Meeting*, vol. 44, 2nd ed. p. 524 (Abstract) (Jul. 11-14, 2003).
G.P. Wilkinson et al., "Pharmacokinetics, metabolism & glutathione reactivity of SJG-136," *British Journal of Cancer*, vol. 88, Supplement 1 (Abstract) p. s29 (Jul. 2-5, 2003).
A. Kamal et al., "Recent developments in the design, synthesis and structure-activity relationship studies of pyrrolo[2,1-c][1,4]benzodiazepines as DNA-interactive antitumour antibiotics," *Current Medicinal Chemistry—Anti-Cancer Agents*, 2(2): 215-254 (2002).
M.J. Keating et al., "Clinical experience with fludarabine in hemato-oncology," *Hematology and Cell Therapy*, Springer-Verlag, publisher, Supplement 2, No. 38, pp. S83-S91 (1996).
G.A. Goodman et al., "Pharmacological basis of therapeutics," *Goodman and Gilman's Pharmacological Basis of Therapeutics, Chapter 52: Antineoplastic Agents*, Pergamon Press, publisher, p. 1415 (2001).
David E. Thurston et al. "Synthesis of DNA-Interactive Pyrrolo [2,1-c][1,4]benzodiazepines," Chemical Reviews, vol. 94, No. 2, pp. 433-465, 1994.
Ting-Chao Chou "Drug Combination Studies and Their Synergy Quantification Using the Chou-Talalay Method", Cancer Research vol. 70, pp. 440-446, 2010.
Lawrence D. Myer et al. "Optimizing Combination Chemotherapy by Controlling Drug Ratio" Molecular Inventions., vol. 7., Issue No. 4, pp. 216-223, Aug. 2007.
Robert A. Kratzke et al., "Evaluation of In Vitro Chemosensitivity Using Human Lung Cancer Cell Lines", J. of Cellular Biochem. Suppl., vol. 24, pp. 160-164, 1996.
Dr. Pepper et al. "Fludarabine-mediated suppression of the excision repair enzyme ERCC1 contributes to the cytotoxic synergy with the DNA minor groove crosslinking agent SJG-136 (NSC 694501) in chronic lymphocytic leukaemia cells" British Journal of Cancer, vol. 97, pp. 253-259, 2007.

* cited by examiner

Primary Examiner — Jeffrey S Lundgren
Assistant Examiner — Bong-Sook Baek
(74) Attorney, Agent, or Firm — Hunton & Williams LLP

(57) ABSTRACT

The invention concerns the use of a therapeutic composition comprising at least one pyrrolobenzodiazepine derivative combined with fludarabine for treating cancer and more particularly hematological diseases.

20 Claims, 1 Drawing Sheet

THERAPEUTIC COMPOSITIONS CONTAINING AT LEAST ONE PYRROLOBENZODIAZEPINE DERIVATIVE AND FLUDARABINE

FIELD of INVENTION

The present invention relates to the use of a therapeutic composition comprising at least one pyrrolobenzodiazepine derivative in combination and in particular in synergic combination with fludarabine for the treatment of cancer. Such a composition is particularly useful for the treatment of certain hematological diseases. The invention also relates to a method for the treatment of cancer with the pyrrolobenzodiazepine derivative in combination and in particular in synergic combination with fludarabine. Finally the present invention relates to a product comprising a pyrrolobenzodiazepine derivative and fludarabine, as a combination product and in particular as a synergic combination product for a use which is simultaneous, separate, or spread over time, for the treatment of cancer.

BACKGROUND of INVENTION

Chemotherapy and more particularly, combined chemotherapy on the basis of the combination of agents with different action mechanisms, is today an established therapeutic principle for combating cancer. Thus the combination of different anti-tumour agents can be a way of increasing anti-tumour effectiveness when a synergic effect is shown and/or when a reduction in toxicity is observed.

In the present Application, the expression "pyrrolobenzodiazepine derivative" comprises the product of formula (I)

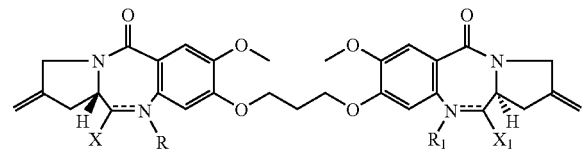

(I)

in which the dotted lines represent a second optional bond between the atoms to which they are attached, and
when a second bond is present between the carbon to which X is attached and the nitrogen atom to which R is attached, then R is absent and X represents hydrogen, or
when there is no second bond between the carbon to which X is attached and the nitrogen atom to which R is attached, then R represents hydrogen and X represents—OH,
and
when a second bond is present between the carbon to which $X_1$ is attached and the nitrogen atom to which $R_1$ is attached, then $R_1$ is absent and $X_1$ represents hydrogen, or
when there is no second bond between the carbon to which $X_1$ is attached and the nitrogen atom to which $R_1$ is attached, then $R_1$ represents hydrogen and $X_1$ represents—OH,
or an addition salt with an acid and/or a solvated form and/or a hydrated form of such a compound, in amorphous or crystalline form, in racemic form or in an optically active form or all combinations of these forms,
and/or any compound which can generate, under physiological conditions, one of the compounds as defined above,
and/or any mixture of some of the compounds or all the compounds listed above.

Another definition of the "pyrrolobenzodiazepine derivative" is as follows: the product of formula (II)

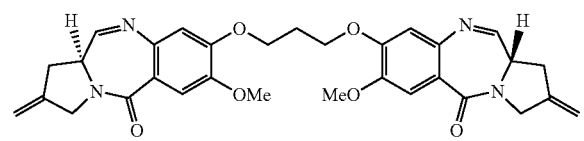

(II)

and/or a mono- and/or bis-carbinol formed by adding water or alcohol,
and/or an addition salt with an acid and/or a solvated form and/or a hydrated form,
and/or an addition salt with an acid and/or a solvated form and/or a hydrated form of such a compound, in amorphous or crystalline form, in racemic form or in an optically active form,
and/or any compound which can generate, under physiological conditions, one of the compounds as defined above,
and/or any mixture of some of the compounds or of all the compounds listed above.

Subsequently, the pyrrolobenzodiazepine derivative as defined above, will be referred to as a "PBD derivative". Such a PBD derivative of this type can be prepared according to the method described in WO 00/12508.

Fludarabine (commercially available in France under the trade name Fludara®) is a product for which the principal therapeutic indications are chronic lymphoid cancers such as chronic lymphoid leukaemia and malignant lymphomas.

DETAILED DESCRIPTION OF THE INVENTION

Figure 1:
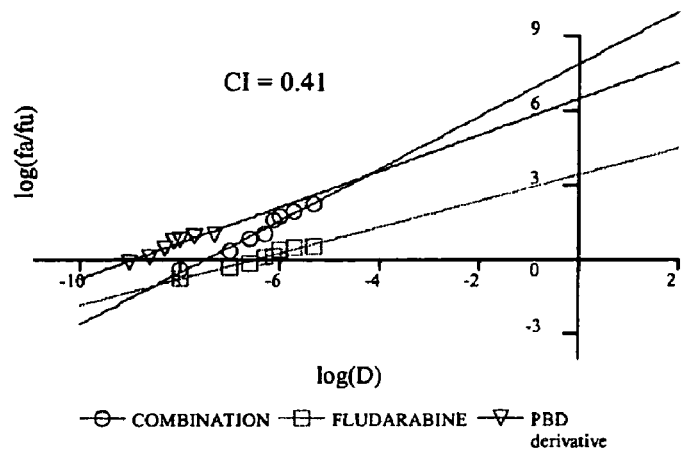
FIG. 1 depicts a dose response curve of PBD derivative, fludarabine, and a combination thereof with a fixed molar ratio of 1/100.

A subject of the present invention is therefore the use of a therapeutic composition comprising at least the PBD derivative in combination with fludarabine, for the preparation of a medicament for the treatment of cancer.

A more particular subject of the present invention is the use as defined above, for the treatment of hematological diseases, preferably for the treatment of leukaemias and very preferably for chronic lymphoid leukaemia.

A subject of the invention is also a cancer treatment method, said method comprising the administration to a patient of a therapeutically or clinically effective dose of a therapeutic composition comprising at least one first compound which is the PBD derivative, and a second compound which is fludarabine. Preferably, such a composition is administered for the treatment of hematological diseases, preferably for the treatment of leukaemias and very preferably for the treatment of chronic lymphoid leukaemia.

Finally, a subject of the present invention is a product comprising the PBD derivative and fludarabine, as a combination product for a use which is simultaneous, separate, or spread over time, for the treatment of cancer. More particularly, a product according to the present invention is suitable for treating hematological diseases, preferably for treating leukaemias and very preferably, chronic lymphoid leukaemia.

A therapeutic composition according to the present invention consists of a combination, and in particular a synergic combination, of the PBD derivative and fludarabine in which the PBD derivative and fludarabine can be present in a non-seperate form and can therefore be administered simultaneously, or in a separate form and thus be administered simultaneously or separately or spread over time. When they are administered separately, the PBD derivative can be administered first or second, with fludarabine respectively second or first.

A composition according to the invention can contain therapeutic agents other than the PBD derivative and fludarabine. Thus, a composition according to the present invention contains the PBD derivative, fludarabine and optionally at least one other therapeutic agent. Preferably, a composition according to the present invention contains the PBD derivative, fludarabine and another therapeutic agent chosen from the monoclonal antibodies. As an example of monoclonal antibodies, rituximab (Rituxano®) or alemtuzumab (Campath®) can be mentioned.

Therapeutic compositions such as those defined above comprise therapeutically effective quantities of the PBD derivative and fludarabine, and a pharmaceutically acceptable support to form together or separately, one liquid composition or compositions such as solutions or suspensions, or one solid composition or compositions such as tablets or powders.

Independently of the administration envisaged, i.e. simultaneous, separate or spread over time, the two compounds, the PBD derivative and fludarabine, can be administered by identical or different administration routes. They can be administered by identical or different administration routes when they are present in the separate form, and by identical administration routes when they are present in the non-separate form. Preferably, the PBD derivative is administered by intravenous route. Fludarabine is administered by the conventionally recommended routes. The other additional agents can be administered by the administration routes recommended in the treatment of cancers.

Preferably, the PBD derivative can be used at a concentration comprised between $1.10^{-11}M$ and $1.10^{-7}M$. Also preferably, the fludarabine can be used at a concentration comprised between $1.10^{-7}M$ and $1.10^{-5}M$.

Preferably, the molar ratio (PBD derivative/fludarabine) is less than 1/250 and more preferably, approximately 1/100 and in particular 1/100.

The PBD derivative can be administered by intravenous route every three weeks at a dose comprised between 1 and 150 µg/m², and preferably between 10 and 100 µg/m².

The activity of a composition according to the present invention can be determined according to the two following protocols: in vitro on human B-CLL cells, in vivo on leukaemia models, and by evaluation of DNA lesions.

Unless otherwise defined, all the technical and scientific terms used in the present Application have the same meaning as that usually understood by a specialist in the field to which the invention belongs.

The following examples are presented in order to illustrate the above procedures and should in no event be considered as a limit to the scope of the invention.

EXPERIMENTAL SECTION

The dose ranges used in this study are as follows:
fludarabine: $1.10^{-7}M$-$1.10^{-5}M$
PBD: $1.10^{-11}M$-$1.10^{-7}M$
derivative With the aim of establishing the appropriate dose range for each therapeutic agent, dose-response curves were produced and the LD50 values were calculated by using a (sigmoidal) non-linear regression analysis method.

In the experiments, chronic lymphoid leukaemia B cells were treated with different dilutions for each of the products taken individually or in combination, but then with a fixed molar ratio.

Analysis of the effects of the combination of the 2 compounds was performed by using the method of Chou and Talalay (Chou T C, Talalay P., Quantitative analysis of dose-response relationships: the combined effects of multiple drugs or enzyme inhibitors. Adv. Enzyme Regul. 1984; 22: 27-55). This method uses dose-response curves for each of the compounds and for a fixed ratio of the 2 compounds, by varying their concentration. Then the combination index (CI) is calculated. A CI value of less than 1 indicates a synergy, and a value of 1 or greater than 1 suggests an additional effect or an antagonism, respectively.

Three molar ratios (PBD derivative/fludarabine) are thus defined: 1/100, 1/250 and 1/500. The value of the combination index obtained for each of these ratios is as follows:

|  | Molar ratio | | |
| --- | --- | --- | --- |
|  | 1/100 | 1/250 | 1/500 |
| CI | 0.41 | 0.93 | 1.42 |

Figure 2:
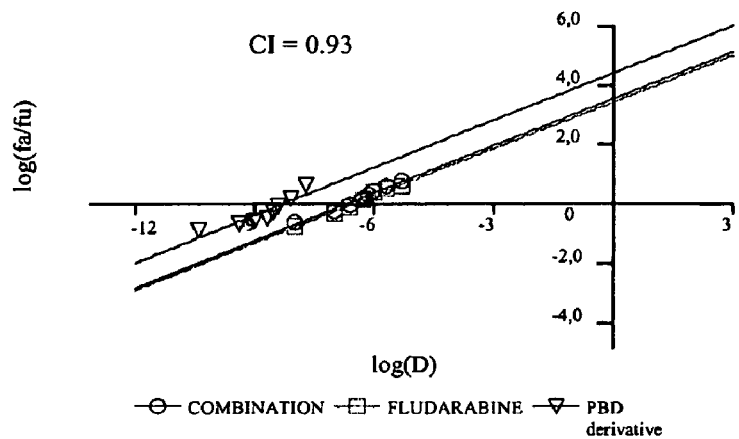
FIG. 2 depicts a dose response curve of PBD derivative, fludarabine, and a combination thereof with a fixed molar ratio of 1/250.
Figure 3:
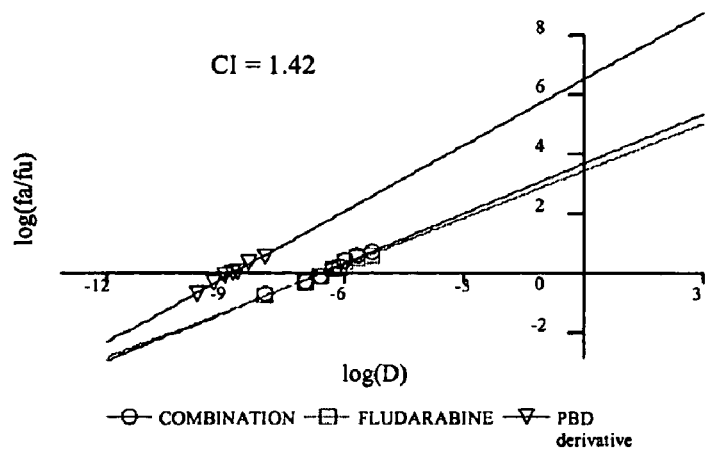
FIG. 3 depicts a dose response curve of PBD derivative, fludarabine, and a combination thereof with a fixed molar ratio of 1/500.

The dose-response curves for the compounds taken individually (PBD derivative and fludarabine) or in combination, with a fixed molar ratio of 1/100, 1/250 and 1/500, are represented by FIGS. 1-3 respectively (fa=fraction affected (apoptosis); fu=fraction unaffected (viable), log D=log of the product concentration).

It should therefore be noted that the molar ratio (PBD derivative: fludarabine) (1/100) gives a combination index value of 0.41, showing that with such a ratio, the combination presents a synergic effect as opposed to the ratio of 1/500 which instead suggests an antagonistic effect.

The invention claimed is:
1. A method of treating a patient who has chronic lymphoid leukemia comprising administering a combination of a compound of formula (I):

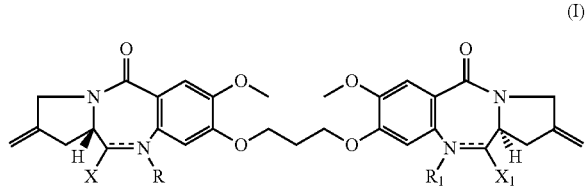

in which the dotted lines represent an optional second bond, and

R is absent and X represents hydrogen when the second bond is present between the carbon to which X is attached and the nitrogen atom to which R is attached, or R represents hydrogen and X represents—OH when there is no second bond between the carbon to which X is attached and the nitrogen atom to which R is attached; and $R_1$ is absent and $X_1$ represents hydrogen when the second bond is present between the carbon to which $X_1$ is attached and the nitrogen atom to which $R_1$ is attached, or $R_1$ represents hydrogen and $X_1$ represents—OH when there is no second bond between the carbon to which $X_1$ is attached and the nitrogen atom to which $R_1$ is attached, or an addition salt thereof, with fludarabine to a patient in need thereof, in a therapeutically synergistic amount exhibiting a combination index of less than one, wherein the combination index is calculated from dose-response curves for the compound of formula (I) and fludarabine on chronic lymphoid leukemia cells.

2. The method of claim 1, comprising administering the compound of formula (I) at a concentration in the range of $1\times10^{-11}$ M and $1\times10^{-7}$ M.

3. The method of claim 1, comprising administering the fludarabine at a concentration between $1\times10^{-7}$ M and $1\times10^{-5}$ M.

4. The method of claim 1, wherein the molar ratio of fludarabine to the compound of formula (I) is approximately 100 to 1.

5. The method of claim 1, wherein the molar ratio of fludarabine to the compound of formula (I) is 100 to 1.

6. The method of claim 1, comprising administering the compound of formula (I) and fludarabine simultaneously.

7. The method of claim 1, comprising administering the compound of formula (I) and fludarabine separately.

8. The method of claim 1, comprising administering the compound of formula (I) and fludarabine spread over time.

9. The method of claim 5, wherein the compound of formula (I) is administered at a concentration between $1\times10^{-11}$ M and $1\times10^{-7}$ M, and the fludarabine is administered at a concentration between $1\times10^{-7}$ M and $1\times10^{-5}$ M.

10. The method of claim 1, comprising administering the compound of formula (I) at a concentration between $1\times10^{-11}$ M and $1\times10^{-7}$ M, and the fludarabine at a concentration between $1\times10^{-7}$ M and $1\times10^{-5}$ M.

11. The method of claim 1, wherein the compound of formula (I) is administered as an amorphous form of the compound.

12. The method of claim 1, wherein the compound of formula (I) is administered as a crystalline form of the compound.

13. The method of claim 1, wherein the compound of formula (I) is administered as a racemic form of the compound.

14. The method of claim 1, wherein the compound of formula (I) is administered as an enantiomeric form of the compound.

15. The method of claim 1, comprising administering the compound of formula (I) where R represents hydrogen and X represents—OH.

16. The method of claim 1, wherein the molar ratio of fludarabine to compound of formula (I) ranges from 250 to 1 to 100 to 1.

17. The method of claim 1, wherein the compound of formula (I) is administered at a dose between 1 and 150 µg/m$^2$.

18. The method of claim 1, wherein the compound of formula (I) is administered at a dose between 10 and 100 µg/m$^2$.

19. The method of claim 1, wherein the therapeutically synergistic amount exhibits a combination index of less than 0.93.

20. The method of claim 15, comprising administering the compound of formula (I) where $R_1$ represents hydrogen and $X_1$ represents—OH.

* * * * *